US010363122B2

(12) United States Patent
Soba (10) Patent No.: US 10,363,122 B2
(45) Date of Patent: Jul. 30, 2019

(54) COMPOSITE MATERIAL FOR MEDICAL DEVICES AND METHOD OF MANUFACTURING THE SAME

(71) Applicant: TERUMO KABUSHIKI KAISHA, Shibuya-ku (JP)

(72) Inventor: Ryoichi Soba, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 257 days.

(21) Appl. No.: 14/088,937

(22) Filed: Nov. 25, 2013

(65) Prior Publication Data

US 2014/0087325 A1 Mar. 27, 2014

Related U.S. Application Data

(63) Continuation of application No. PCT/JP2012/061712, filed on May 8, 2012.

(30) Foreign Application Priority Data

May 26, 2011 (JP) .................................. 2011-118434

(51) Int. Cl.
*A61F 2/01* (2006.01)
*A61C 7/20* (2006.01)
(Continued)

(52) U.S. Cl.
CPC ........ *A61F 2/013* (2013.01); *A61B 17/12113* (2013.01); *A61C 7/20* (2013.01); *A61F 2/82* (2013.01); *A61L 31/124* (2013.01); *A61L 31/14* (2013.01); *A61M 25/09* (2013.01); *B22F 3/20* (2013.01); *C22C 1/10* (2013.01); *C22C 32/001* (2013.01); *C22C 32/0021* (2013.01); *C22C 32/0026* (2013.01); *C22C 32/0031* (2013.01);
(Continued)

(58) Field of Classification Search
CPC ... A61C 7/20; A61C 2201/007; A61F 2/2418; A61F 2/07; A61F 2210/0014; A61B 2017/00867
USPC .......................... 29/896.11; 433/20; 623/1.15
See application file for complete search history.

(56) References Cited

U.S. PATENT DOCUMENTS

| | | | |
|---|---|---|---|
| 4,389,250 A * | 6/1983 | Melton | ................. C22C 1/0425 420/486 |
| 2002/0190841 A1* | 12/2002 | Chiba | ..................... C22C 19/07 338/296 |

(Continued)

FOREIGN PATENT DOCUMENTS

| | | |
|---|---|---|
| CN | 101407867 A | 4/2009 |
| CN | 101440439 A | 5/2009 |

(Continued)

OTHER PUBLICATIONS

International Search Report (PCT/ISA/210) dated Aug. 7, 2012, by the Japanese Patent Office as the International Searching Authority for International Application No. PCT/JP2012/061712.
(Continued)

*Primary Examiner* — Matthew M Nelson
(74) *Attorney, Agent, or Firm* — Buchanan Ingersoll & Rooney PC (57) ABSTRACT

A composite material for medical devices includes a superelastic shape memory alloy configured or constituting a matrix and a metal oxide which is dispersed in the matrix.

11 Claims, 4 Drawing Sheets

(51) Int. Cl.
    *A61L 31/12*     (2006.01)
    *A61L 31/14*     (2006.01)
    *C22C 32/00*     (2006.01)
    *A61B 17/12*     (2006.01)
    *A61F 2/82*     (2013.01)
    *A61M 25/09*     (2006.01)
    *B22F 3/20*     (2006.01)
    *C22C 1/10*     (2006.01)

(52) U.S. Cl.
    CPC ....... *A61L 2400/16* (2013.01); *A61L 2430/36* (2013.01); *B22F 2998/10* (2013.01)

(56) References Cited

U.S. PATENT DOCUMENTS

2004/0117001 A1* 6/2004 Pelton .................. A61F 2/91
    623/1.15
2006/0228536 A1* 10/2006 Chernyshov ............ A61L 27/06
    428/304.4

FOREIGN PATENT DOCUMENTS

| JP | 58-34103 A | 2/1983 |
|---|---|---|
| JP | 63-190130 A | 8/1988 |
| JP | 09-118967 A | 5/1997 |
| JP | 09-182799 A | 7/1997 |
| JP | 2000-17395 A | 1/2000 |
| JP | 2000017395 A * | 1/2000 |
| JP | 2002-105561 A | 4/2002 |
| JP | 2002-105565 A | 4/2002 |
| JP | 2003-325655 A | 11/2003 |
| WO | WO 2010/051515 A1 | 5/2010 |

OTHER PUBLICATIONS

Chinese Office Action dated Apr. 16, 2015, by the Chinese Patent Office in corresponding Chinese Patent Application No. 201280025134.8 (8 pgs).

European Search Report dated Jun. 16, 2015, by the European Patent Office in corresponding European Patent Application No. 12790246.8-1351 (7 pages).

Second Office Action dated Dec. 18, 2015 by the Chinese Patent Office in corresponding Chinese Patent Application No. 201280025134. 8, and an English translation thereof (15 pages).

Khalil-Allafi et al., "Biocompatibility and corrosion behavior of the shape memory NiTi alloy in the physiological environments simulated with body fluids for medical applications", Material Science and Engineering C, Elsevier Oct. 12, 2010, vol. 30, No. 8, pp. 1112-1117, XP027265932.

The extended European Search Report dated Nov. 17, 2015, by the European Patent Office in corresponding European Application No. 12790246.8. (15 pages).

Official Action dated Oct. 13, 2015 by the Japanese Patent Office in corresponding Japanese Patent Application No. 2013-516269.

Office Action (Communication pursuant to Article 94(3) EPC) dated May 8, 2018, by the European Patent Office in corresponding European Patent Application No. 12 790 246.8-1101. (6 pages).

* cited by examiner

COMPOSITE MATERIAL FOR MEDICAL DEVICES AND METHOD OF MANUFACTURING THE SAME

CROSS REFERENCES TO RELATED APPLICATIONS

This application is a continuation of International Application No. PCT/JP2012/061712 filed on May 8, 2012, and claims priority to Japanese Application No. 2011-118434 filed on May 26, 2011, the entire content of both of which is incorporated herein by reference.

TECHNICAL FIELD

The present invention generally relates to a composite material which is used for medical devices such as stents, guide wires, embolization coils, inferior vena cava filters, and wires for orthodontics, and particularly relates to a composite material for medical devices utilizing a superelastic shape memory alloy as a matrix and a method of manufacturing the same.

BACKGROUND DISCUSSION

Various kinds of alloys have been used as the material for medical devices such as stents and guide wires. For example, Japanese Application Publication No. 2003-325655 discloses a stent consisting of NiTi shape memory alloys and Japanese Application Publication No. 9-182799 discloses a guide wire consisting of NiTi-based alloys, CuZnAl-based alloys, CuAlNi-based alloys, or the like.

NiTi-based alloys, FeMnSi-based alloys, CuAlNi-based alloys, CuZnAl-based alloys, or the like are generally called a shape memory alloy, and among these, there is an alloy showing superelasticity at human body temperature (around 37° C.). The superelastic shape memory alloys have a crystal structure in which stress-induced type martensitic transformation is generated and have characteristics of returning to their original shape after releasing the stress. The term, "superelasticity" herein means that even if the material is deformed (bent, stretched, compressed, and twisted) at service temperature to the region in which ordinary metals undergo plastic deformation, releasing the deformation stress results in recovery to nearly the original shape before deformation without heating. The superelastic shape memory alloys having such characteristics can be used with advantage in stents, guide wires, or the like which are used in the living body.

Since the superelastic shape memory alloys are generally a "soft" alloy, there were some cases where the stress value in the plateau region (the region in which the stress value shows nearly constant value with respect to an increase of strain in the stress-strain curve) is insufficient depending on the application. In particular, in medical devices such as stents and guide wires which are arranged or used in the living body, more reduction in size is desired. However, when the stress value in the plateau region (the strength) is insufficient, it is difficult to promote a reduction in size such as a reduction in wall thickness and a reduction in diameter.

SUMMARY

According to one aspect disclosed here, a medical device composite material comprises a superelastic shape memory alloy constituting a matrix; and a metal oxide dispersed in the matrix.

According to another aspect, a medical device comprises: one of a stent, a guide wire, an embolization coil, an inferior vena cava filter, and an orthodontics wire made of a composite material comprising a superelastic shape memory alloy matrix in which a metal oxide is dispersed.

The medical device composite material exhibits improved stress value in the plateau region. A description will be set forth below of various Examples implementing the composite material disclosed here. Generally, speaking, the stress value in the plateau region is improved by containing the proper dose of the metal oxide in the matrix.

To contain the proper dose of the metal oxide in the matrix, the composite material for medical devices is preferably obtained by sintering to be subjected to extrusion processing after the superelastic shape memory alloy powder and the metal oxide particles are mixed. If the metal oxide particles are added into the dissolved superelastic shape memory alloys, it is difficult to maintain the proper dose of the metal oxide in the matrix. In contrast, if the metal oxide particles are added into and mixed with the superelastic shape memory alloy powder, it is possible to maintain the proper dose of the metal oxide in the matrix.

The additive amount of the metal oxide particles to the superelastic shape memory alloy powder is preferably from 0.10% by volume to 1.0% by volume. When the additive amount is less than 0.10% by volume, an improvement of the stress value in the plateau region is insufficient. When the additive amount is over 1.0% by volume, while the stress value in the plateau region is improved, it does not become appropriate for the application as medical devices used in the living body since a decrease in stretching becomes prominent.

Furthermore, "the additive amount of the metal oxide to the superelastic shape memory alloy powder" defined by % by volume is part by volume of the additive amount of the metal oxide to 100 part by volume of the superelastic shape memory alloy powder.

The superelastic shape memory alloy powder is, for example, one kind of alloy powder selected from a group consisting of TiNi-based alloy powder, Cu-based alloy powder, Fe-based alloy powder, and Ti-based alloy powder. As a material for medical devices such as stents and guide wires, TiNi-based alloys which have excellent biocompatibility are particularly preferable. TiNi-based alloys have excellent corrosion resistance in the blood, and there is no risk that the alloy constituents are eluted into the blood since the surface is stable. The metal oxide particles are, for example, one kind of oxide particles selected from a group consisting of $TiO_2$, $Al_2O_3$, $CeO_2$, MgO, CaO and $ZrO_2$.

In a preferred embodiment, the superelastic shape memory alloy powder is TiNi-based alloy powder, and the metal oxide particles and the additive amount thereof are any one of 0.10% by volume to 1.0% by volume of $TiO_2$ and 0.1% by volume to 1.0% by volume of $Al_2O_3$.

Another aspect involves a method of manufacturing a medical device composite material used to fabricate medical devices. The method comprises: producing an ingot consisting of a superelastic shape memory alloy using a dissolution method; crushing or cutting the superelastic shape memory alloy ingot to produce a superelastic shape memory alloy powder; mixing the superelastic shape memory alloy powder and metal oxide particles; and sintering a mixture of the superelastic shape memory alloy powder and the metal oxide particles to be subjected to extrusion processing.

In the method described above, it is preferable that the superelastic shape memory alloys be TiNi-based alloys, and the metal oxide and the additive amount thereof are any one of 0.10% by volume to 1.0% by volume of $TiO_2$ and 0.1% by volume to 1.0% by volume of $Al_2O_3$.

According to the material and method disclosed here, in a composite material for medical devices utilizing a superelastic shape memory alloy as a matrix, it is possible to improve the stress value in the plateau region in the stress-strain curve by containing a metal oxide which is dispersed in the matrix. As a result, it is possible to realize a reduction in wall thickness and a reduction in diameter, of medical devices such as stents and guide wires.

DETAILED DESCRIPTION

A composite material disclosed here is used for medical devices such as stents, guide wires, embolization coils, inferior vena cava filters, and wires for orthodontics, and contains a metal oxide which is dispersed in the matrix, utilizing a superelastic shape memory alloy as a matrix.

The superelastic shape memory alloys have the alloy constituents which can exhibit superelastic shape memory characteristics, and for example, TiNi-based alloys, Cu-based alloys, Fe-based alloys, Ti-based alloys, and the like can be included. In a case of TiNi-based alloys, TiNi-based alloys contain 43% by mass to 57% by mass of Ni and the residue consists of Ti and unavoidable impurities. A small amount of other metals, for example, cobalt, iron, palladium, platinum, boron, aluminum, silicon, vanadium, niobium, copper, or the like may be added to such TiNi-based alloys.

As Cu-based alloys, for example, CuAlNi alloys, CuZn alloys, CuZnAl alloys, and the like can be included. As Fe-based alloys, for example, FeNi alloys, FeMnSi alloys, FePd alloys, FePt alloys, and the like can be included. As Ti-based alloys, for example, TiNb alloys, TiMo alloys, and the like can be included.

Among the various kinds of the superelastic shape memory alloys described above, the superelastic shape memory alloys which are particularly appropriate as a composite material for medical devices are TiNi-based alloys in which the strain recovery is large and which have excellent biocompatibility. An example of TiNi-based alloys is TiNi-based alloys, for example, in which TiNi-based alloys contain 54.5% by mass to 57% by mass of Ni and the residue consists of Ti and unavoidable impurities. As unavoidable impurities, 0.050% by mass or less of Co, 0.010% by mass or less of Cu, 0.010% by mass or less of Cr, 0.005% by mass or less of H, 0.050% by mass or less of Fe, or 0.050% by mass or less of Nb may be contained.

To improve the stress value in the plateau region in the stress-strain curve, it is important to disperse the metal oxide in the matrix of the superelastic shape memory alloys. Examples of the metal oxide include $TiO_2$, $Al_2O_3$, $CeO_2$, MgO, CaO and $ZrO_2$, and the like. A preferred metal oxide is any one of $TiO_2$ and $Al_2O_3$.

The proper dose of the metal oxide should be contained in the matrix, but it has been found that if the metal oxide particles such as $TiO_2$ and $Al_2O_3$ are added into the dissolved superelastic shape memory alloy, it is difficult to maintain the proper dose of the metal oxide in the matrix.

The composite material disclosed here is manufactured through the following steps. The following description will be set forth using as an example a case where the superelastic shape memory alloys are TiNi-based alloys.

(A) Production of an Ingot

An ingot consisting of TiNi-based alloys is produced by a dissolution method. As an other method, it is considered that a sintered body of TiNi-based alloy is obtained by a powder metallurgy method in which Ti powder and Ni powder are mixed to be sintered.

(B) Production of TiNi-Based Alloy Powder

TiNi-based alloy powder is obtained by crushing or cutting the TiNi-based alloy ingot.

(C) Addition of a Metal Oxide

Metal oxide particles such as $TiO_2$ and $Al_2O_3$ are added to TiNi-based alloy powder to mix so that metal oxide particles are uniformly dispersed. The additive amount of metal oxide particles to TiNi-based alloy powder is preferably 0.10% by volume to 1.0% by volume. If the additive amount is less than 0.10% by volume, an improvement of the stress value in the plateau region is insufficient in the stress-strain curve in the composite material which is finally obtained. When the additive amount is over 1.0% by volume, while the stress value in the plateau region is improved, it is not appropriate for the application as medical devices used in the living body, since a decrease in stretching becomes prominent. Particularly, in a case of stents being arranged at a bending part of the blood vessel, the characteristic of stretching becomes an important factor, since a cyclic bending load acts.

(D) Sintering and Extrusion Processing

The mixture of the TiNi-based alloy powder and the metal oxide particles is sintered to be subjected to extrusion processing. Sintering is preferably performed in a vacuum atmosphere or an inert gas atmosphere, and more preferably performed in a vacuum atmosphere. The sintering temperature is not particularly limited. However, by way of example, 700° C. to 1,200° C. is preferable, and 800° C. to 1,100° C. is more preferable. In addition, extrusion processing is preferably hot extrusion processing.

After steps described above, the composite material for medical devices according to the disclosure here is obtained. In the composite material which is finally obtained, for example, by dispersing $Al_2O_3$ as particles in the matrix of TiNi-based alloys, the strength of the composite material is enhanced. In this manner, if $Al_2O_3$ particles are added, it is possible to improve the stress value in the plateau region of the composite material which is finally obtained, by strengthening particle dispersion. However, there is a possibility that a particle dispersion strengthening type composite material may not be appropriate for applications in which a cyclic bending load acts. For example, in a case of manufacturing stents which are to be being arranged at a bending part of the blood vessel using a particle dispersion type composite material, the presence of particles dispersed in the matrix of a device which is to be subjected to cyclic loading is likely to be the starting point of fatigue failure.

In a case of the application described above, it is preferable that $TiO_2$ particles be used as metal oxide particles. In a case where metal oxide particles which are added are $TiO_2$, $TiO_2$ are not finally present as particles but by decomposing, oxygen is dissolved in a parent phase to provide solid solution strengthening and the strength of the composite material for medical devices is improved. Particularly, by adding $Tio_2$ particles not by a melting method (a dissolution method), but by a powder metallurgy method, it is possible to dissolve more oxygen content. Since oxygen which is dissolved does not become the starting point of fatigue failure, an oxygen solid solution strengthening type composite material is appropriate for the application in which a cyclic load is applied.

As a metal oxide where the solid solution strengthening of oxygen can be expected, $CeO_2$, $MgO$, $CaO$, $ZrO_2$, and the like in which it is considered that it is more difficult to decompose than $TiO_2$, from an oxide standard production free energy diagram, can be included. In these metal oxides, without oxygen which has been decomposed once reacting to a metal element to generate a metal oxide again, oxygen is dissolved in a parent phase.

The applications of the composite material of the invention are medical devices such as stents, guide wires, embolization coils, inferior vena cava filters, and wires for orthodontics. While being described in Examples later, in a case of TiNi-based alloy composite material to which 0.5% by volume (0.33 wt %) of $TiO_2$ particles are added, the stress value (the strength) in the plateau region increases from 600 MPa (no addition of $TiO_2$) to 800 MPa. Therefore, considering an application for stents having a conventional material thickness (wall thickness) of the material forming the stent of 0.2 mm, the material thickness can be reduced to approximately three-quarter (about 1.5 mm) if the same degree of the strength is maintained. One benefit of reducing the material thickness is that the amount of the used alloys is decreased and as a result, it is possible to reduce elution of alloy constituents since it is possible to support a film of the blood vessel by a thin beam. In addition, when delivering to the blood vessel, it is possible to fold stents into a smaller diameter.

Considering that the stress value (the strength) in the plateau region increases form 600 MPa to 800 MPa, considering an application for guide wires, the outer diameter of 0.50 mm of the conventional wires can be reduced to 0.45 mm if the same degree of strength is maintained. One benefit of this reduction in diameter is that it is possible to achieve the reduction in diameter of the inner and outer diameter of other medical devices which can be laid along wires.

EXAMPLES

Preparation of a Mixture

The following mixtures were prepared.
Sample 1: TiNi-based alloy powder (Comparative Example)
Sample 2: 0.5% by volume (0.33 wt %) of $TiO_2$ particles are added to TiNi-based alloy powder (Example of the invention)
Sample 3: 1.0% by volume (0.66 wt %) of $TiO_2$ particles are added to TiNi-based alloy powder (Example of the invention)
Sample 4: 0.2% by volume of $Al_2O_3$ particles are added to TiNi-based alloy powder (Example of the invention)
Sample 5: 1.0% by volume of $Al_2O_3$ particles are added to TiNi-based alloy powder (Example of the invention)
Sample 6: 0.15% by volume (0.10 wt %) of $TiO_2$ particles are added to TiNi-based alloy powder (Example of the invention)
Sample 7: 0.38% by volume (0.25 wt %) of $TiO_2$ particles are added to TiNi-based alloy powder (Example of the invention)

Sintering

Figure 5:
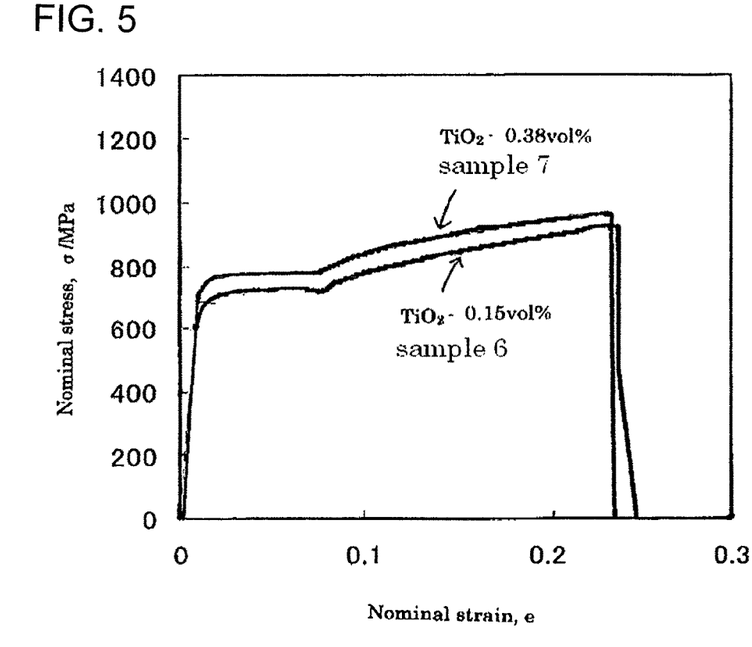
FIG. 5 is a graph illustrating the results of tensile tests for an extruded product of TiNi-based alloys to which 0.15% by volume (0.1 wt %) of $TiO_2$ particles are added (Sample 6), and an extruded product of TiNi-based alloys to which 0.38% by volume (0.25 wt %) of $TiO_2$ particles are added (Sample 7).

Each sample described above was sintered according to the following conditions to obtain a sintered body.
Temperature: 900° C.
Retention time: 30 minutes
Atmosphere: Vacuum
Pressure: 40 MPa
Rate of temperature elevation: 20° C./min Hot Extrusion Processing The sintered body obtained was subjected to hot extrusion processing according to the following conditions to obtain an extruded product.
Preheating temperature: 1,050° C.
Pre-overheating time: 10 minutes
Extrusion ratio: 6
Extrusion ram speed: 6 mm/sec Tensile Test Tensile tests of the extruded products of Samples 1 to 7 were performed at ambient temperature under the following conditions, with tensile tests conducted on two products of each of the Samples 1 to 5, and on one product of each of Samples 6 and 7.
Shape of test piece: Round bar
Diameter of test piece: 3.5 mm
Length of test piece: 20 mm
Tension speed: Strain rate $5 \times 10^{-4} s^{-1}$ FIGS. 1, 2 and 5 illustrate the test results of Sample 1, Sample 2 and Sample 3, the test results of Sample 1, Sample 4 and Sample 5, and the test results of Sample 6 and Sample 7, respectively.

Figure 1:
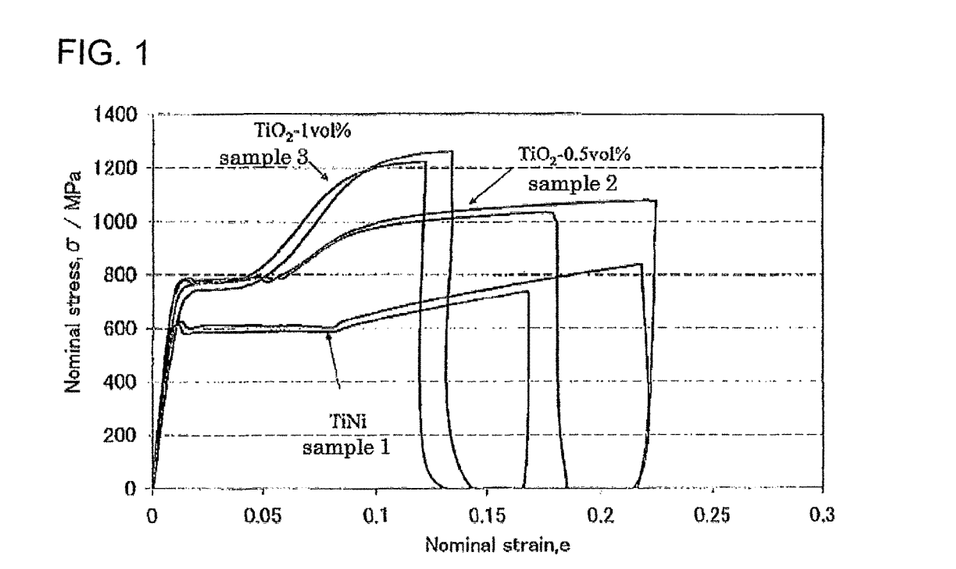
FIG. 1 is a graph illustrating the results of tensile tests for an extruded product of TiNi-based alloys to which a metal oxide is not added (Sample 1), an extruded product of TiNi-based alloys to which 0.5% by volume (0.33 wt %) of $TiO_2$ particles are added (Sample 2), and an extruded product of TiNi-based alloys to which 1.0% by volume (0.66 wt %) of $TiO_2$ particles are added (Sample 3).
Figure 2:
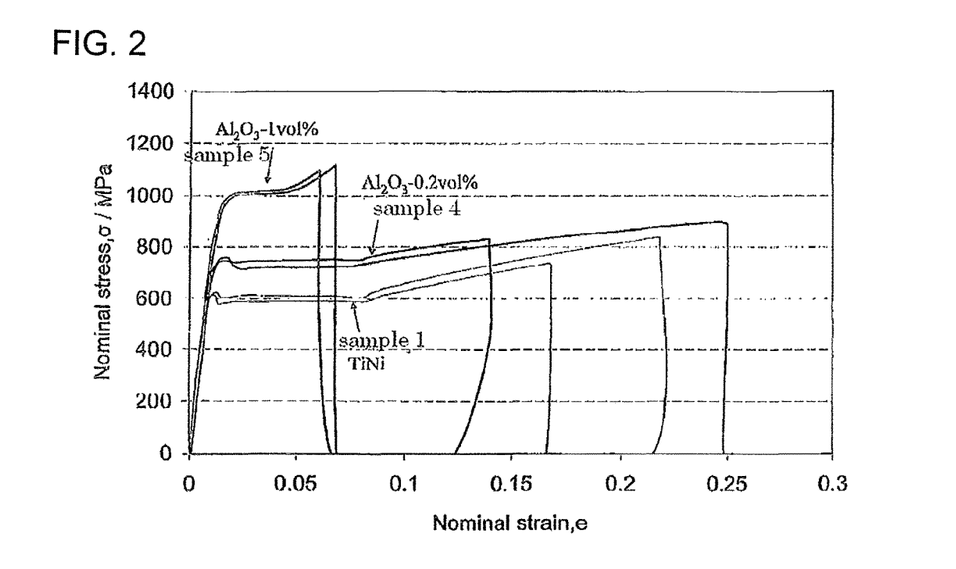
FIG. 2 is a graph illustrating the results of tensile tests for an extruded product of TiNi-based alloys to which a metal oxide is not added (Sample 1), an extruded product of TiNi-based alloys to which 0.2% by volume of $Al_2O_3$ particles are added (Sample 4), and an extruded product of TiNi-based alloys to which 1.0% by volume of $Al_2O_3$ particles are added (Sample 5).

The graph illustrated in FIG. 1 shows that in Sample 2 to which 0.5% by volume (0.33 wt %) of $TiO_2$ was added and Sample 3 to which 1.0% by volume (0.66 wt %) of $TiO_2$ was added, the stress values in the plateau region in the stress-strain curve are improved as compared to Sample 1 to which $TiO_2$ was not added. In addition, as the additive amount of $TiO_2$ increases, the breaking strength also improved. On the other hand, regarding elongation characteristics, it is recognized that Sample 3 to which 1.0% by volume of $TiO_2$ was added is deteriorated as compared to Sample 1 and Sample 2.

Considering medical device applications such as stents and guide wires, since deteriorating elongation characteristics are typically not very much desired, the preferred upper limit value of the additive amount of $TiO_2$ is 1.0% by volume.

The stress value of Sample 1 to which $TiO_2$ was not added in the plateau region is about 600 MPa, whereas the stress value of Sample 2 to which 0.5% by volume (0.33 wt %) of $TiO_2$ was added in the plateau region is about 800 MPa.

Regarding elongation characteristics, a big difference between Sample 1 and Sample 2 is not recognized.

From the graph illustrated in FIG. 5, the stress value of Sample 6 to which 0.15% by volume (0.10 wt %) of $TiO_2$ was added in the plateau region is about 720 MPa, the stress value of Sample 7 to which 0.38% by volume (0.25 wt %) of $TiO_2$ was added in the plateau region is about 770 MPa, and the stress values are significantly improved as compared to Sample 1 to which $TiO_2$ was not added. Regarding elongation characteristics, big difference among Sample 1, Sample 6 and Sample 7 are not recognized.

It is discovered that the preferred additive amount of $TiO_2$ is from approximately 0.15% by volume (0.10 wt %) to 0.5% by volume (0.33 wt %), from the viewpoint of improving the stress value in the plateau region without deteriorating elongation characteristics. Considering that the stress value in the plateau region increases by about 120 MPa when the additive amount of $TiO_2$ is 0.15% by volume (0.10 wt %), an increase in the stress value by about 100 MPa is expected even if 0.10% by volume is added. Therefore, the preferred lower limit value of the additive amount of $TiO_2$ is 0.10% by volume.

The graph illustrated in FIG. 2 shows that in Sample 4 to which 0.2% by volume of $Al_2O_3$ was added and Sample 5 to which 1.0% by volume of $Al_2O_3$ was added, the stress values and the breaking strength in the plateau region in the stress-strain curve are improved as compared to Sample 1 to which $Al_2O_3$ was not added. The stress values and the breaking strengths in the plateau region increase in proportion to the additive amount of $Al_2O_3$. Regarding elongation characteristics, it is recognized that Sample 5 to which 1.0% by volume of $Al_2O_3$ was added exhibits deteriorated elongation characteristics as compared to Sample 1 and Sample 4.

Considering medical device applications, since deteriorating elongation characteristics are typically not very much desired, the preferred upper limit value of the additive amount of $Al_2O_3$ is 1.0% by volume.

The stress value of Sample 1 to which $Al_2O_3$ was not added in the plateau region is about 600 MPa, whereas the stress value of Sample 4 to which 0.2% by volume of $Al_2O_3$ was added in the plateau region is about 750 MPa. Regarding elongation characteristics, a big difference between Sample 1 and Sample 4 is not recognized. It is thus discovered that the preferred additive amount of $Al_2O_3$ is approximately 0.2% by volume, from the viewpoint of improving the stress value in the plateau region without deteriorating elongation characteristics. Considering that the stress value in the plateau region increases by about 150 MPa when the additive amount of $Al_2O_3$ is 0.2% by volume, an increase in the stress value by about 100 MPa is expected even 0.1% by volume is added. Therefore, the preferred lower limit value of $Al_2O_3$ is 0.1% by volume.

Hysteresis Test

Using a tensile test in which the stress is released after imparting a constant strain by stretching the extruded products of Sample 2, Sample 3, Sample 6 and Sample 7 to form a cycle, a hysteresis test in which three cycles are performed by changing the strain imparted was performed according to the following conditions. The strain amount of Sample 2 is set to 3% at cycle 1, 7% at cycle 2, and 15% at cycle 3. The strain amount of Sample 3 is set to 3% at cycle 1, 5% at cycle 2, and 10% at cycle 3. The strain amount of Sample 6 and Sample 7 is set to 4% at cycle 1, 10% at cycle 2, and 15% at cycle 3.

Figure 3:
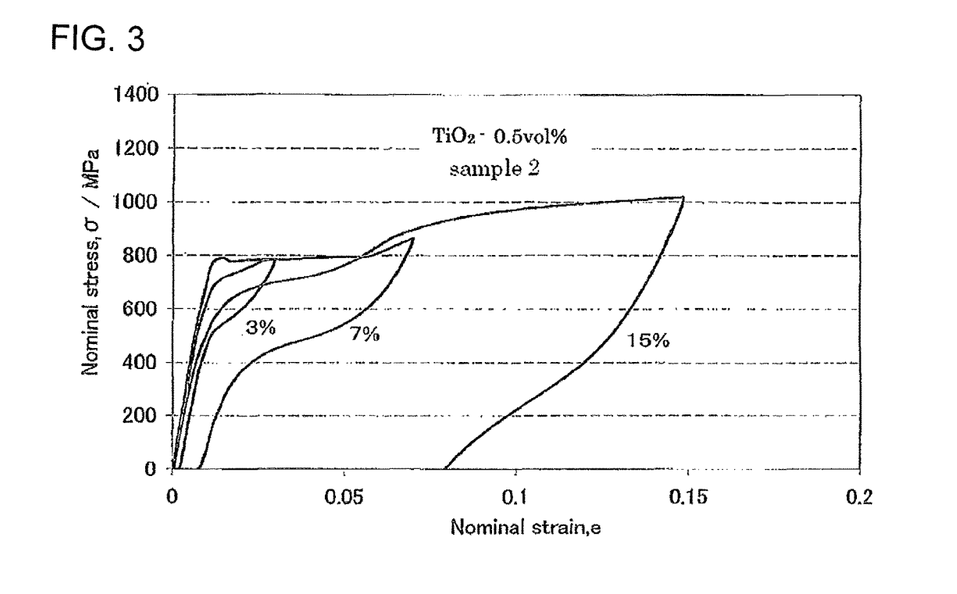
FIG. 3 is a graph illustrating the result of hysteresis test for Sample 2.
Figure 4:
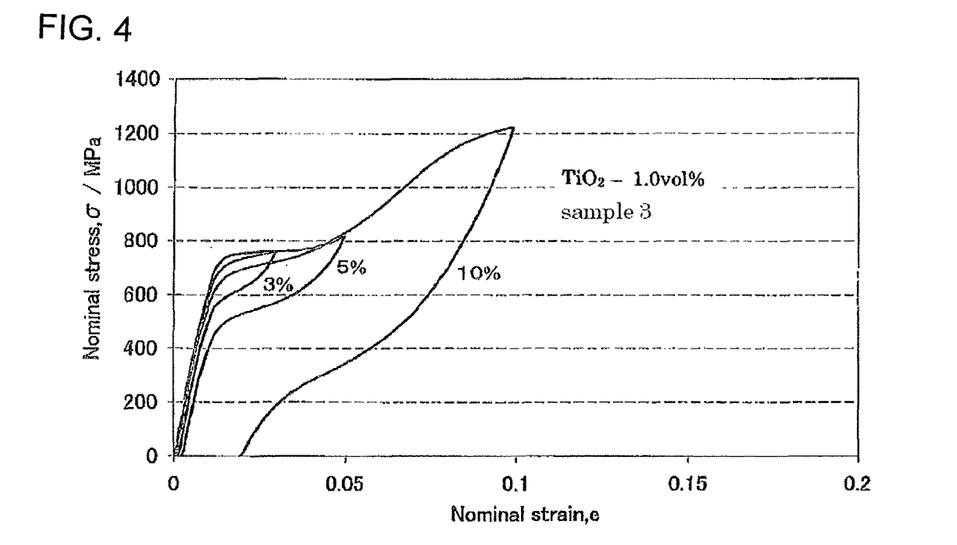
FIG. 4 is a graph illustrating the result of hysteresis test for Sample 3.
Figure 6:
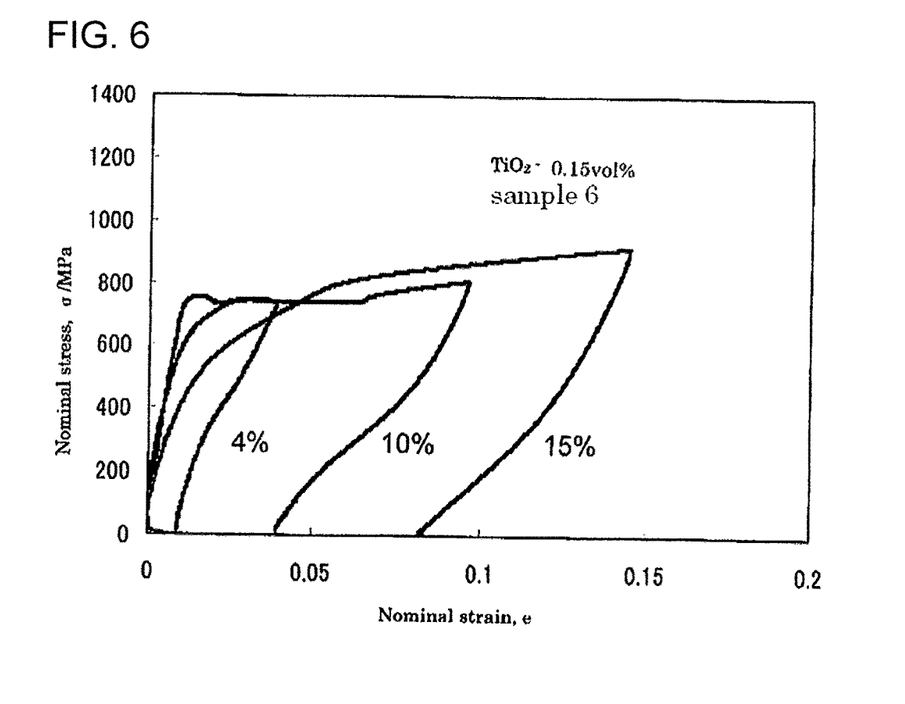
FIG. 6 is a graph illustrating the result of hysteresis test for Sample 6
Figure 7:
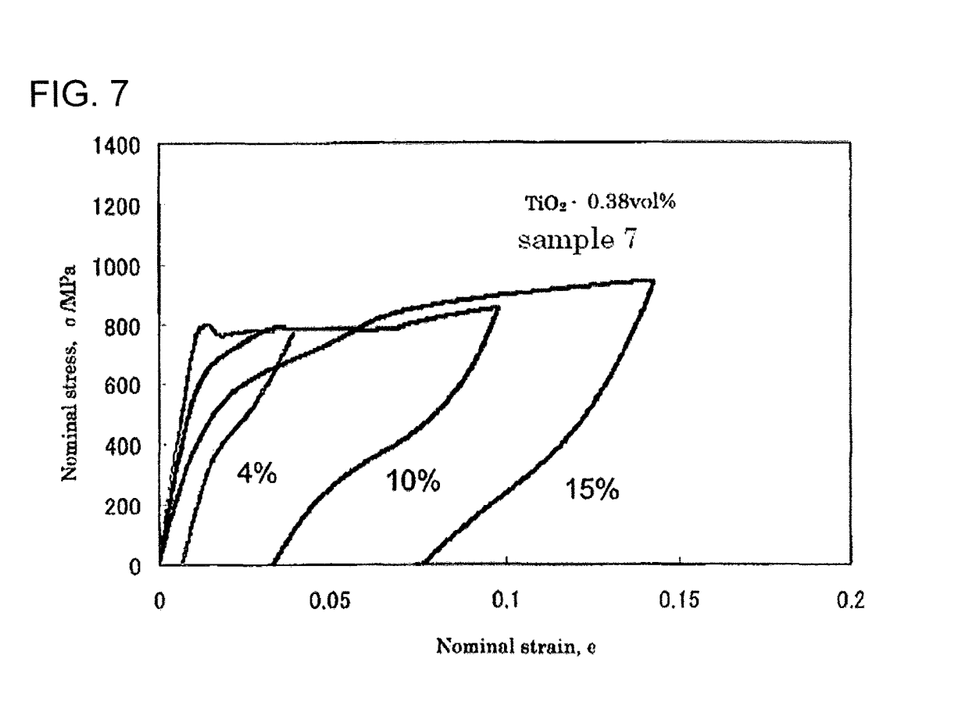
FIG. 7 is a graph illustrating the result of hysteresis test for Sample 7.

Shape of test piece: Round bar
Diameter of test piece: 3.5 mm
Length of test piece: 20 mm
Tension speed: Strain rate $5 \times 10^{-4} s^{-1}$ The result of Sample 2 is illustrated in FIG. 3, the result of Sample 3 is illustrated in FIG. 4, the result of Sample 6 is illustrated in FIG. 6, and the result of Sample 7 is illustrated in FIG. 7. From these FIGS., it is discovered that after releasing the stress, the strain deformation returns to some extent in Sample 2, Sample 3, Sample 6, and Sample 7 to which $TiO_2$ was added.

The composite material disclosed here has useful application as a material for medical devices such as stents and guide wires.

The detailed description above describes a composite material having useful application for medical devices. The invention is not limited, however, to the precise embodiment and variations described. Various changes, modifications and equivalents can be employed by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
one of a stent, a guide wire, an embolization coil, an inferior vena cava filter, and an orthodontics wire made of a composite material comprising a superelastic shape memory alloy matrix in which a metal oxide is dispersed;
wherein the superelastic shape memory alloy matrix is a sintered body made from a superelastic shape memory alloy powder, and the metal oxide is metal oxide particles dispersed in the superelastic shape memory alloy powder in an amount from 0.10% by volume to 0.5% by volume, and wherein the metal oxide particles are any one of 0.15% by volume to 0.5% by volume of $TiO_2$ and 0.10% by volume to 0.2% by volume of $Al_2O_3$; and
wherein the superelastic shape memory alloy powder is a TiNi-based alloy powder.

2. The medical device according to claim 1, wherein the TiNi-based alloy powder contains 54.5% by mass to 57% by mass of Ni and a residue consists of Ti and unavoidable impurities.

3. The medical device according to claim 2, wherein the unavoidable impurities consists of 0.050% by mass or less of Co, 0.010% by mass or less of Cu, 0.010% by mass or less of Cr, 0.005% by mass or less of H, 0.050% by mass or less of Fe, or 0.050% by mass or less of Nb.

4. The medical device according to claim 1, wherein the metal oxide particles are $TiO_2$ dispersed in the superelastic shape memory alloy powder in an amount from 0.15% by volume to 0.5% by volume.

5. The medical device according to claim 1, wherein the metal oxide particles are $Al_2O_3$ dispersed in the superelastic shape memory alloy powder in an amount of approximately 0.2% by volume.

6. A medical device composite material, comprising:
a superelastic shape memory alloy constituting a matrix;
a metal oxide dispersed in the matrix;
wherein the superelastic shape memory alloy matrix is a sintered body made from a superelastic shape memory alloy powder, and the metal oxide is metal oxide particles dispersed in the superelastic shape memory alloy powder in an amount from 0.10% by volume to 0.5% by volume, and wherein the superelastic shape memory alloy powder is TiNi-based alloy powder, and the metal oxide particles and the additive amount thereof are any one of 0.15% by volume to 0.5% by volume of $TiO_2$ and 0.10% by volume to 0.2% by volume of $Al_2O_3$; and wherein the superelastic shape memory alloy powder is a TiNi-based alloy powder.

7. The medical device composite material according to claim 6, wherein the medical device composite material is obtained by sintering the superelastic shape memory alloy powder and the metal oxide comprised of the metal oxide particles.

8. The medical device composite material according to claim 6, wherein the TiNi-based alloy powder contains 54.5% by mass to 57% by mass of Ni and a residue consists of Ti and unavoidable impurities.

9. The medical device composite material according to claim 8, wherein the unavoidable impurities consists of 0.050% by mass or less of Co, 0.010% by mass or less of Cu, 0.010% by mass or less of Cr, 0.005% by mass or less of H, 0.050% by mass or less of Fe, or 0.050% by mass or less of Nb.

10. The medical device composite material according to claim 6, wherein the metal oxide particles are $TiO_2$ dispersed in the superelastic shape memory alloy powder in an amount from 0.15% by volume to 0.5% by volume.

11. The medical device composite material according to claim 6, wherein the metal oxide particles are $Al_2O_3$ dispersed in the superelastic shape memory alloy powder in an amount of approximately 0.2% by volume.

* * * * *